(12) United States Patent
Hermanne

(10) Patent No.: US 9,504,409 B2
(45) Date of Patent: Nov. 29, 2016

(54) DEVICE AND METHOD FOR DETECTING RESPIRATORY MOVEMENTS

(71) Applicant: 2-Observe s.a., Ferrieres (BE)

(72) Inventor: Jean-Philippe Hermanne, Vyle et Tharoul (BE)

(73) Assignee: 2-OBSERVE S.A. (BE)

( * ) Notice: Subject to any disclaimer, the term of this patent is extended or adjusted under 35 U.S.C. 154(b) by 194 days.

(21) Appl. No.: 14/401,445

(22) PCT Filed: May 14, 2013

(86) PCT No.: PCT/EP2013/059863
§ 371 (c)(1),
(2) Date: Nov. 14, 2014

(87) PCT Pub. No.: WO2013/171178
PCT Pub. Date: Nov. 21, 2013

(65) Prior Publication Data
US 2015/0148683 A1 May 28, 2015

(30) Foreign Application Priority Data

May 14, 2012 (BE) .................................. 2012/0319

(51) Int. Cl.
*A61B 5/00* (2006.01)
*A61B 5/113* (2006.01)
*A61B 5/11* (2006.01)

(52) U.S. Cl.
CPC .............. *A61B 5/113* (2013.01); *A61B 5/1126* (2013.01); *A61B 5/1135* (2013.01); *A61B 5/7207* (2013.01); *A61B 5/746* (2013.01); *A61B 5/725* (2013.01); *A61B 5/7214* (2013.01); *A61B 2560/0247* (2013.01)

(58) Field of Classification Search
CPC .................... A61B 2560/0247; A61B 5/1126; A61B 5/113; A61B 5/1135; A61B 5/7207; A61B 5/7214; A61B 5/725; A61B 5/746
See application file for complete search history.

(56) References Cited

U.S. PATENT DOCUMENTS

| 4,745,284 A | 5/1988 | Masuda et al. |
| 5,309,921 A | 5/1994 | Kisner et al. |
| 2008/0269625 A1 | 10/2008 | Halperin et al. |

FOREIGN PATENT DOCUMENTS

| BE | WO 2005/020815 A1 | 3/2005 |
| GB | WO 03/005893 A2 | 1/2003 |

*Primary Examiner* — Mark Remaly
(74) *Attorney, Agent, or Firm* — Richards Patent Law P.C.

(57) ABSTRACT

The invention relates to a method for determining the presence of a respiratory movement in a human or an animal. This method comprises the detection of a movement by a passive infrared detector and the analysis of signals transmitted by this detector. The invention also relates to an apparatus for executing a method of detecting a respiratory movement.

13 Claims, 5 Drawing Sheets

DEVICE AND METHOD FOR DETECTING RESPIRATORY MOVEMENTS

TECHNICAL FIELD

The invention relates to a method for monitoring the respiration of a human or animal patient by analyzing infrared radiation received by at least one passive infrared detector. The invention also relates to a device for monitoring the respiration of a human or animal patient.

PRIOR ART

For many years, research has been undertaken in the field of devices and methods for detecting respiratory problems, notably those occurring during sleep, such as bradypnea, hypopnea or apnea. Accordingly, many devices have been developed to detect respiratory problems and to monitor the respiration rate of a person or an animal over a longer or shorter period of time. However, the current devices and methods have a number of drawbacks. Some are invasive, in that they require physical contact with the person or the animal, which may be troublesome for the person or animal, or may even be incompatible with the presence of other devices used in a hospital or veterinary environment. For example, the polysomnography apparatus described in US20100331632 has to be strapped around the person or animal for the detection of respiratory problems. Other devices require no physical contact, but either they are expensive, or they are devices emitting radiation, such as electromagnetic radiation, with a potentially pathogenic effect on the human or animal body which cannot be disregarded; similarly, the possibility of interference with other medical apparatus cannot be disregarded when this type of apparatus is used in a hospital or veterinary setting.

WO2005020815 describes the use of passive infrared detectors in the context of a method for monitoring the respiration rate of a person or an animal. High-sensitivity passive infrared detectors are positioned around the person or animal. These apparatus detect the movements of the rib cage, and transmit the data related to these movements to an amplifier via a logic controller. The amplifier is itself connected to an alarm. If any of the detectors detects no movement during a certain period of time, this alarm is triggered, so that the person can be wakened, or another person can be alerted about this event.

However, although this device is useful and has well-established advantages, it is not entirely satisfactory because of the number of false positives and false negatives that it generates. Because of their high sensitivity, infrared detectors receive considerable background noise which often makes the signals unusable and generates false data, and this is incompatible with a device intended to aid the detection of major physiological problems, such as the presence of respiratory arrest of the central apnea type with multiple etiologies. It has proved to be very difficult to distinguish signals generated by a movement of the rib cage from signals generated by the environment. The determination of the presence or absence of thoracic expansion by a simple, arbitrarily chosen detection threshold may lead to numerous errors.

BRIEF DESCRIPTION OF THE INVENTION

One object of the present invention is to resolve, at least partially, the problems associated with the monitoring of the respiration of a person or animal. Notably, this is achieved by proposing a device and a method for detecting respiratory movements, which require no contact with the person or animal, and provide more reliable detection of the presence or absence of a respiratory movement.

To this end, the method for monitoring the respiration of a patient according to the invention is characterized in that it comprises the following steps:
  providing at least one passive infrared detector targeting at least one location on the patient capable of exhibiting respiratory movements,
  providing, at a sampling frequency fE, at least one sequence of discrete measurement signals originating from the at least one passive infrared detector,
  defining a series of N sliding time windows, starting at different successive moments $T_{in,i}$, where i is an integer from 1 to N representing each sliding time window with a length of $\Delta T_i = T_{f,i} - T_{in,i}$, where $T_{f,i}$ denotes a final time of a sliding time window numbered i,
  subtracting from each of said discrete measurement signals present in the same sliding time window a continuous component calculated over a plurality of these discrete measurement signals present in the same sliding time window, to obtain at least one temporal sequence of useful discrete signals,
  generating at each final time $T_{f,i}$ an indicator of respiratory movements, calculated on the basis of a mean amplitude calculated over a set of useful discrete signals included in a sliding time window with a length of $\Delta T_i$ preceding said time $T_{f,i}$ of the sliding time window numbered i.

This method can be used to analyze discrete measurement signals providing at least one passive infrared detector targeting at least one location on the patient capable of exhibiting respiratory movements, and to provide better discrimination between erroneous movement detections and real detections. This method can also be used to analyze low-amplitude signals when high background noise is present. Thus the detection of an absence of respiratory movement takes place with high accuracy, and the alarm is not triggered inopportunely.

In a particular embodiment of the invention, the method includes a step of calculating a mean amplitude, consisting in:
  calculating an RMS value of a set of useful discrete signals included in a sliding time window with a length of $\Delta T_i$,
  comparing said RMS value with a predefined threshold of detection of a respiratory movement, by the calculation of a mean amplitude.

The method according to this embodiment can be used to compare, for each sliding time window, the mean amplitude of a set of useful discrete signals in said time window in question with predefined values, thus further improving the detection sensitivity of the method.

In another particular embodiment of the invention, the method includes a step of spectral analysis of a set of useful discrete signals included in a sliding time window, followed by the determination of the two highest peaks present in the spectral analysis of the set of useful discrete signals included in said sliding time window, followed by a step of comparison of the frequency of the highest peak with a specified frequency range, followed by the calculation of a coefficient for determining the presence or absence of a respiratory movement. As a result of this embodiment, if a set of useful discrete signals is not sufficiently distinguished from the signals generated by background noise and transmitted by the at least one passive infrared detector targeting at least one location on the patient capable of exhibiting respiratory movements, it is possible to classify a set of useful discrete signals included in a sliding analysis window, thus further improving the sensitivity of the method for detecting the presence or absence of a respiratory movement.

The invention is also applicable to a device for detecting the presence or absence of a respiratory movement in a person or animal.

These aspects and other aspects of the invention will be clarified in the detailed description of particular embodiments of the invention.

BRIEF DESCRIPTION OF THE DRAWINGS

Reference will be made to the drawings of the figures, in which.

The drawings in the figures are not to scale. In most cases, similar elements are denoted by similar references in the figures. The presence of reference numerals in the drawings is not to be considered as limiting, even where these numerals are mentioned in the claims.

DEFINITIONS

A measurement signal is a signal directly generated by a passive infrared detector. A measurement signal may be filtered and/or amplified. A discrete measurement signal is a measurement signal that is transmitted to an apparatus for processing a signal at a specified sampling frequency. A useful discrete signal is a discrete measurement signal included in a sliding time window from which the continuous component of said discrete measurement signal has been subtracted.

The term "passive infrared detector" is to be interpreted as meaning a detector that can detect infrared radiation emitted by a radiant heat transfer, but cannot transmit this radiation. However, a passive infrared detector according to the invention may transmit radiation of the type transmitted according to a Wi-Fi or ZigBee protocol for the transmission of data relating to detected and measured infrared radiation. An example of a passive infrared detector may be a detector comprising two pyroelectric elements sensitive to infrared radiation. The two pyroelectric elements receive infrared radiation and supply a signal proportional to the quantity of infrared radiation received. A quantity differential between the infrared radiation received by each of the pyroelectric elements of the same passive infrared detector is calculated by said detector, and said detector generates an electrical signal which is the measurement signal. Typically, it is when a movement of a human or animal body takes place in the field of detection of a passive infrared sensor that a differential exists between the two pyroelectric elements of the same passive infrared detector. When a human or animal body moves, the two pyroelectric elements do not receive the same quantity of infrared radiation. A passive infrared detector therefore converts a movement into an electrical signal.

DETAILED DESCRIPTION OF PARTICULAR EMBODIMENTS

Figure 1:
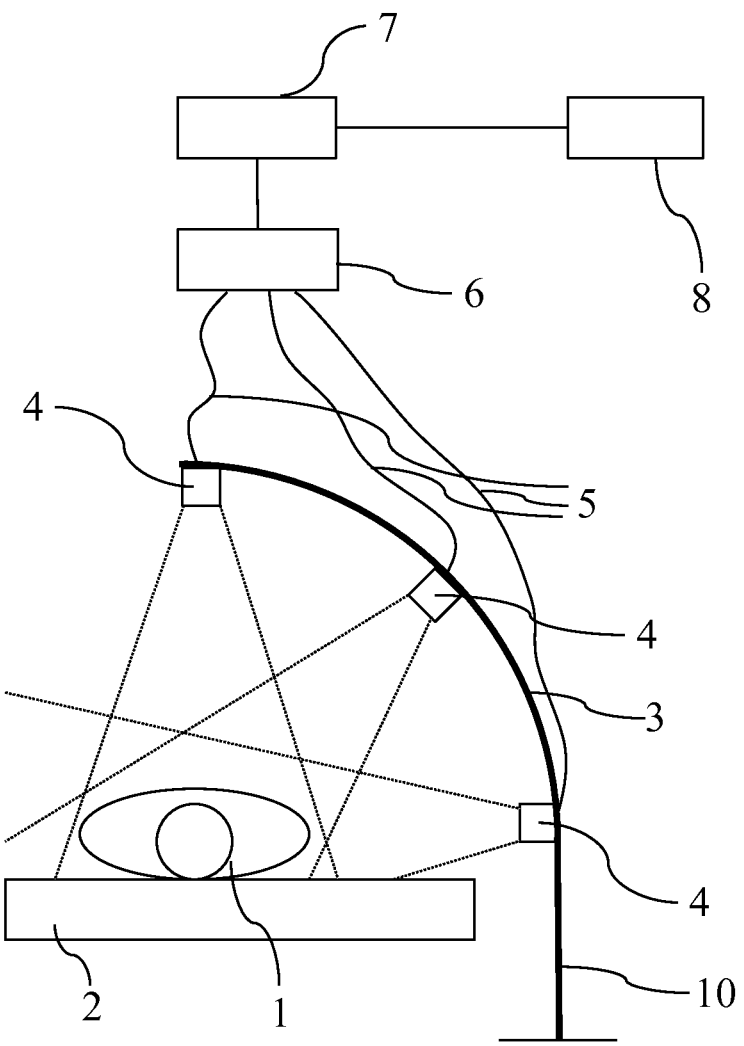
FIG. 1 shows, in a schematic manner, a device according to the invention.

Reference will be made initially to FIG. 1 which represents a device according to the invention. At least a part of the device can be fastened to a base (9) in the proximity of a bed (2) where the person (1) to be monitored is located. At least a part of the device can also be arranged on a supplementary structure fixed to a bed (2) and/or incorporated into the structure of the bed (2) itself. This part of the device comprises at least one passive infrared detector (4) targeting at least one location on the patient capable of exhibiting respiratory movements, such as the rib cage or the abdomen, for example. The device can also comprise a curved support (3) intended to support at least one passive infrared detector (4). Preferably, a passive infrared detector (4) is a detector comprising at least two piezoelectric sensors (a "dual sensor" detector), and even more preferably it comprises at least four piezoelectric sensors (a "quad sensor" detector), a piezoelectric sensor being an element sensitive to passive infrared radiation. According to these embodiments, the detection of a respiratory movement is even more sensitive when a plurality of piezoelectric elements are present. Furthermore, when a passive infrared detector (4) comprises at least four piezoelectric sensors, the problems related to the directional sensitivity of the detectors can be reduced. The passive infrared detector or detectors (4) are connected by connecting means (5) to a differential amplifier (6). The differential amplifier (6) is connected to a signal processing means (7). The signal processing means (7) is connected to a visual and/or audible alarm means (8) located close to or at a distance from the device.

Since respiratory movements are low-amplitude movements, the at least one passive infrared detector (4) can be supplemented by a means for concentrating the incident infrared radiation toward the pyroelectric elements in order to improve the sensitivity of the passive infrared detectors (4). A means of this type may be, for example, a Fresnel lens or a segmented parabolic lens. A means of this type enables the incoming useful signal to be concentrated toward the pyroelectric elements of a passive infrared detector (4). These means are well known to persons skilled in the art and will not be described further. Alternatively, it is possible to add to the at least one passive infrared detector (4) a lens for detecting the radiation present in a central area of the detector while simultaneously detecting radiation present at the periphery of the detector. For example, a wide-field lens, such as a lens for detecting radiation present in a field of the passive infrared detector in the range from −90° to +90° in the horizontal field, and from −84° to +84° in the vertical field, may be used. A lens of this type makes it possible to avoid the presence of a blind field (there is no detection of any variation of infrared radiation in the blind field) in a detection field of a passive infrared detector (4).

The passive infrared detector (4) may also be enhanced to provide increased sensitivity to low-amplitude movements. The detector (4) is thus more sensitive to movements, and its detection dynamics are improved. The sensitivity of the detector may thus be in the range from 0.1 to 10 $V_{pp}$, more preferably from 3 to 4.5 $V_{pp}$, and even more preferably from 3.3 to 3.6 $V_{pp}$.

There is no limit to the number of passive infrared detectors (4) that can be included in the device. The number may be, for example, 1, 2, 3, 4, 5, 6, 7, 8, 9 or 10 detectors. The number of detectors may be in the range from 1 to 10, from 1 to 9, from 1 to 8, or from 3 to 6. Preferably, the number of detectors is six, distributed in three housings, each comprising two passive infrared detectors (4). The distance between the passive infrared detectors (4) and the location on the body of a person or animal capable of exhibiting periodic movements associated with respiration may be in the range from 20 cm to 200 cm, or preferably from 25 cm to 150 cm. The positioning of the passive infrared detectors (4) around the location on the body of a person or animal that is capable of exhibiting periodic movements associated with respiration may conform to a 90° arc of a circle (3), as shown in FIG. 1. The expression "targeting at least one location on the patient capable of exhibiting respiratory movements" is to be interpreted as meaning that the location on the patient capable of exhibiting respiratory movements is in the detection field of the at least one passive infrared detector (4). The detection field of a passive infrared detector (4) is generally a cone with an aperture in the range from 30° to 70°. This field may be modified by the addition of lenses as explained above.

Figure 2:
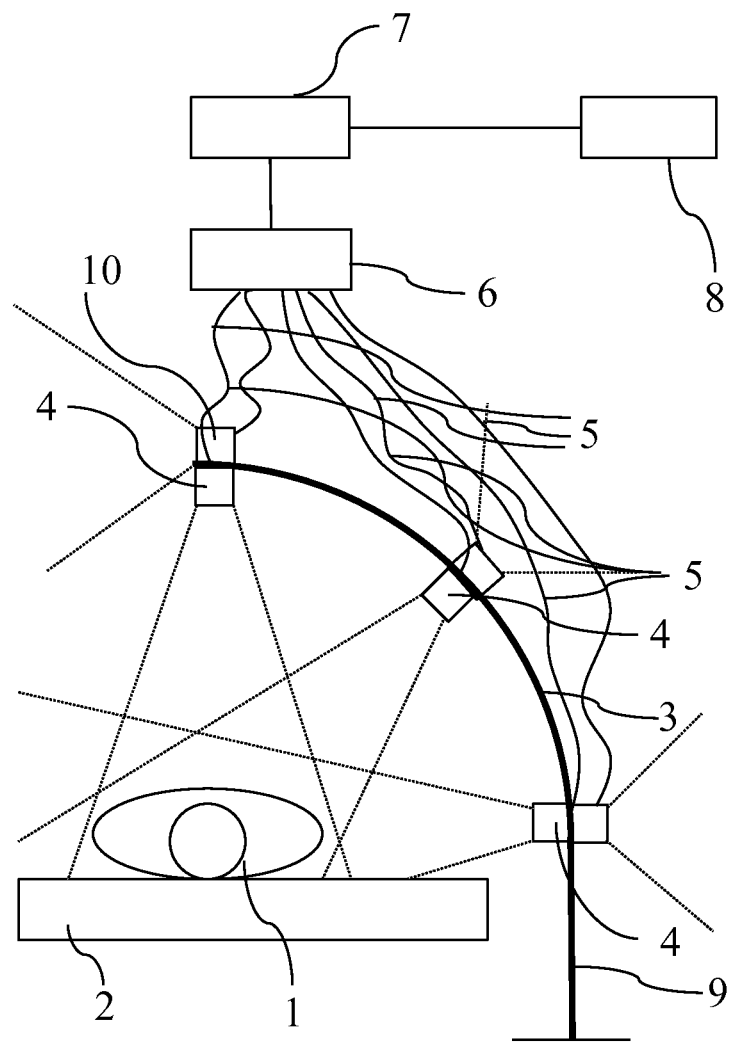
FIG. 2 shows, in a schematic manner, a particular embodiment of a device according to the invention.

Since respiratory movements are low-amplitude movements, the measurement signal leaving the at least one passive infrared detector may be of low amplitude. A differential signal amplifier (6) for a passive infrared detector can be used. This amplifier is connected to the at least one passive infrared detector (4) by conventional connecting means (5) placed between an amplifier (6) and a passive infrared detector (4). Each passive infrared detector (4) is connected to the amplifier (6). The amplifier (6) is connected to a signal processing means (7). An analog/digital converter may also be provided between the amplifier (6) and the signal processing means (7). These amplifiers (6) are well known in the prior art. A differential amplifier (6) may be, for example, an operational amplifier. The signal processing means (7) is connected to a visual and/or audible alarm (8). According to a preferred embodiment of the invention, as shown in FIG. 2, an additional passive infrared detector (10), targeting the environment of the patient (1), or a part of the patient (1) not capable of exhibiting movements related to respiration, is provided. The signal processing means may be an analog and/or digital signal processing means. Preferably, the signal processing means is a digital means.

Figure 3:
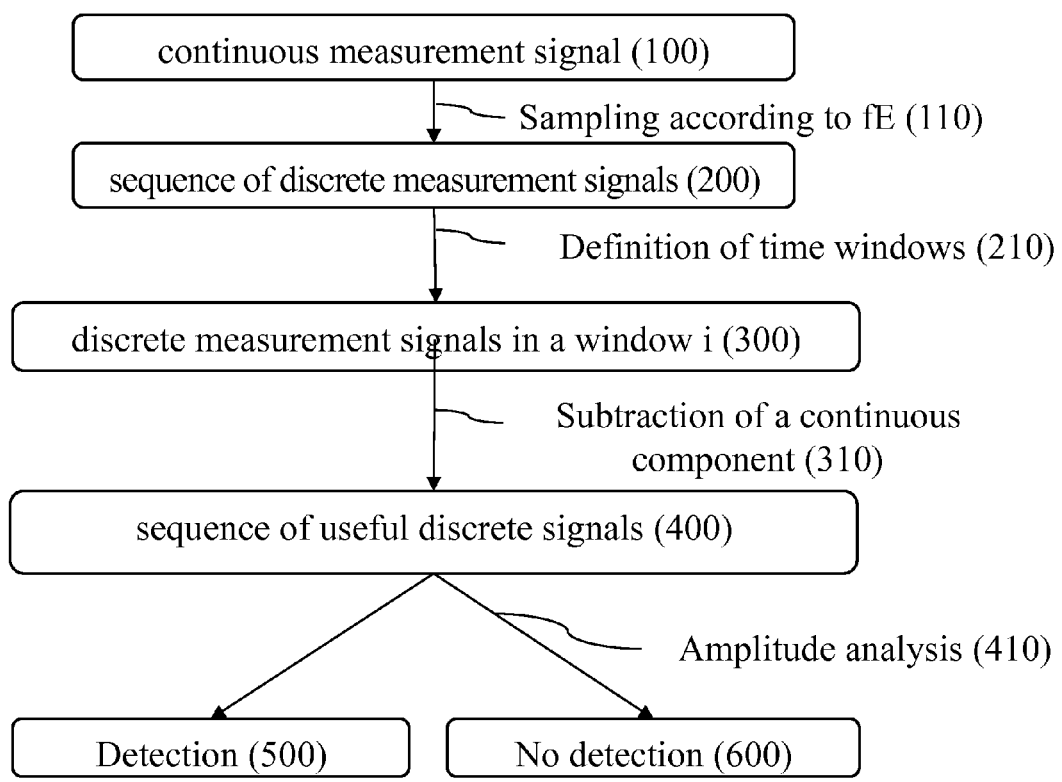
FIG. 3 shows, in a schematic manner, various steps of a method for applying the invention.

Reference will now be made to FIG. 3. The method for monitoring the respiration of a patient comprises the following steps:
i) providing at least one passive infrared detector targeting at least one location on the patient capable of exhibiting respiratory movements,
ii) providing, at a sampling frequency fE (110), at least one sequence of discrete measurement signals (200) originating from the at least one passive infrared detector,
iii) defining a series of N sliding time windows (210), starting at different successive moments where i is an integer from 1 to N representing each sliding time window with a length of $\Delta T_i = T_{f,i} - T_{in,i}$ where $T_{f,i}$ denotes a final time of a sliding time window numbered i,
iv) subtracting from each of said discrete measurement signals present in the same sliding time window (300) a continuous component (310) calculated over a plurality of these discrete measurement signals (300) present in the same sliding time window, to obtain at least one temporal sequence of useful discrete signals (400),
v) generating at each final time $T_{f,i}$ an indicator of respiratory movements (410), calculated on the basis of a mean amplitude calculated over a set of useful discrete signals (400) included in a sliding time window with a length of $\Delta T_i$ preceding said time $T_{f,i}$ of the sliding time window numbered i.

The at least one passive infrared detector targeting at least one location on the patient capable of exhibiting respiratory movements detects the movements of a heat source in a continuous manner, and converts this movement to a continuous measurement signal (100). This continuous measurement signal (100) is transmitted by the at least one passive infrared detector (4) to an amplifier (6), the latter transmitting the amplified signal to the signal processing means (7). The transmission of the measurement signals takes place at a specified sampling frequency fE (110), thus converting a continuous measurement signal (100) to a sequence of discrete measurement signals (200). This step is therefore a sampling of a continuous measurement signal (100), enabling a sequence of discrete measurement signals (200) to be obtained, this sequence being composed of a plurality of signal measurements detected at a plurality of successive moments, at a specified sampling frequency fE (110). This frequency fE may, for example, be in the range from 0.1 to 100 hertz. Preferably, this frequency may be in the range from 0.1 to 50 hertz. Even more preferably, this frequency may be in the range from 1 to 10 hertz. Also more preferably, the frequency fE is 10 hertz. Preferably, a range of wavelengths transmitted by the at least one passive infrared detector (4) can be selected, in order to transmit only a part of the infrared radiation. Thus, a continuous measurement signal (100) can be transmitted solely for wavelengths in the range from 8 μm to 14 μm. This wavelength selection may be carried out by means of an optical filter, provided in the at least one passive infrared detector (4), and/or by the provision of a filter at the piezoelectric sensor of the at least one passive infrared detector (4), enabling the piezoelectric sensor to transmit only the signals corresponding to wavelength variations in the range from 8 μm to 14 μm. Also preferably, a range of particular frequencies can be amplified. Thus, it is preferable to amplify only the signals whose frequency is in the range from 0.01 Hz to 10 Hz, and even more preferably from 0.01 Hz to 7 Hz. According to this preferred embodiment, only the signals present in the defined frequency window are amplified, these signals representing the useful signal, because they represent the frequency of the respiratory movement. The signals present outside this amplification window are therefore not amplified, thus enabling the further analysis of the useful signal to be improved, because these signals represent phenomena other than a respiratory movement. It is possible to select the signals having a wavelength in the range from 0.01 Hz to 10 Hz, or more preferably from 0.01 Hz to 7 Hz, by providing a low-pass filter (for retaining only the signals having a frequency below a specified upper limit) and a low-pass filter (for retaining only the signals having a frequency higher than the specified lower limit). The radiation selected in this way is then amplified by means of an operational amplifier. It is also possible to define a cut-off frequency for the signal amplification process, with the aim of improving the subsequent resolution of the transmitted signal. The aim of this operation is to avoid the presence of noise in the transmitted signal. In order to avoid this noise, any signal whose frequency exceeds a predetermined value is not taken into account in the subsequent analysis of the signal.

If more than one passive infrared detector (4) targeting at least one location on the patient (1) capable of exhibiting respiratory movements is present, each of the passive infrared detectors (4) targeting at least one location on the patient (1) capable of exhibiting respiratory movements detects the respiratory movements in a continuous manner, and converts this movement to a continuous measurement signal (100). Each of the continuous measurement signals (100) is transmitted at the same specified sampling frequency fE (110), thus converting all the continuous measurement signals (100) to the same number of sequences of discrete measurement signals (200). Each of the sequences of discrete measurement signals (200) is then analyzed separately.

The series of discrete measurement signals (200) may be processed as they are transmitted to the signal processing means (7) during the monitoring of a person (1), but they may also be stored for later analysis.

Figure 5A:
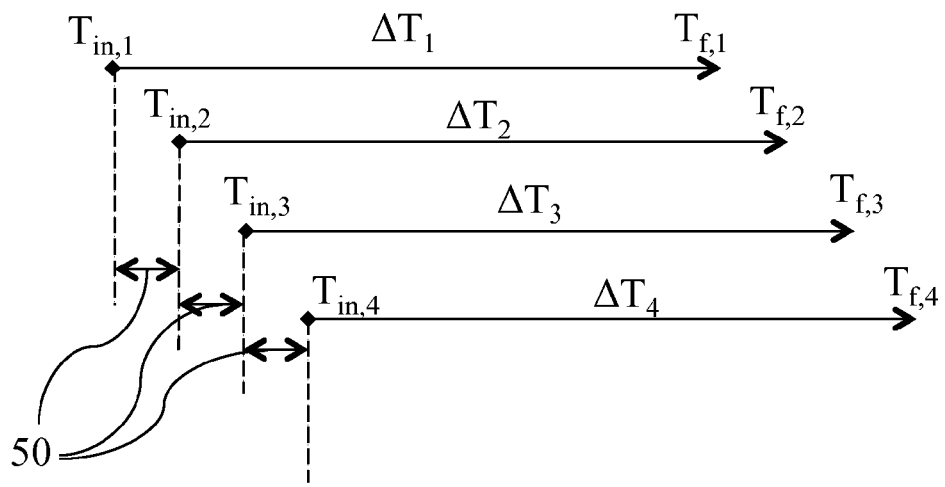
FIG. 5a shows, in a schematic manner, a superimposition of sliding time windows with a length of $\Delta T_i$, separated by a constant time interval.

The method comprises a step of defining a series of N sliding time windows (210), starting at different successive moments $T_{in,i}$ where i is an integer from 1 to N representing each sliding time window, with a length of $\Delta T_i = T_{f,i} - T_{in,i}$, where $T_{f,i}$ denotes a final time of a sliding time window numbered i. N is an integer greater than 0. This step of the method is shown in FIG. 5a. A sliding window i is delimited by boundaries ($T_{in,i}$ and $T_{f,i}$) sliding in time according to a specified time interval (50). The length $\Delta T_i$ of a sliding time window may be defined as a function of a duration of a patient's normal respiratory cycle. This window must be no shorter than the duration of the patient's normal respiratory cycle, in order to provide a periodic characteristic in the series of discrete measurement signals (200). This sliding time window must not be too long, in order to enable an absence of respiratory movement to be detected as soon as possible. This window must not be less than the inverse of the sampling frequency fE ($\Delta T_i > 1/fE$). For example, in the case of an adult human, if the duration of the person's normal respiratory cycle is 5 seconds, a sliding time window may be in the range from 5 seconds to 20 seconds, or preferably from 10 seconds to 15 seconds. Sliding time windows follow each other according to a specified time interval. A time interval may, for example, be in the range from 0.5 second and 4 seconds; it may also be in the range from 0.5 to 2 seconds. Preferably, the time interval between each time window is 1 second. Each sliding time window therefore comprises a set of discrete measurement signals (200), the number of which depends on the duration of the length $\Delta T_i$ of the sliding time window and on the sampling frequency fE. Preferably, the sliding time windows have a constant length $\Delta T_i$, but it is possible to have sliding time windows with a variable length $\Delta T_i$. The method therefore comprises a step of determining time windows which follow each other and may overlap, in order to obtain an indicator of respiratory movement in each time window, where said time windows may overlap, may follow each other, and/or may be spaced apart in time. Thus the time windows that are defined permit the continuous monitoring of the respiration of a patient or an animal.

Figure 5B:
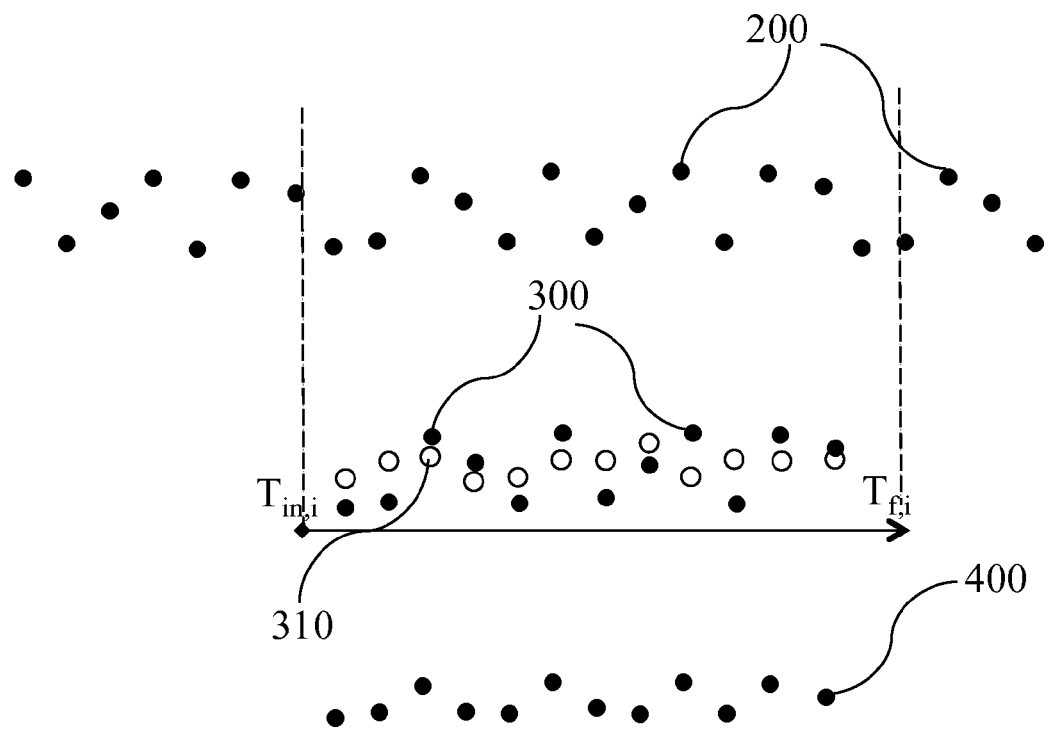
FIG. 5b shows, in a schematic manner, some steps of a method for applying the invention.

The method comprises a step which, for each sliding time window, consists in subtracting from each of said discrete measurement signals present in the same sliding time window (300) a continuous component (310) calculated over a plurality of these discrete measurement signals present in the same sliding time window (300), to obtain at least one temporal sequence of useful discrete signals (400). This step of the method is shown in FIG. 5b. A continuous component (310) of a set of discrete measurement signals of a given window (300) may, for example, be calculated by replacing each discrete measurement signal with a moving mean calculated over a plurality of discrete measurement signals of the same time window (300). For example, the number of discrete measurement signals to be taken into account in order to define a continuous component can be determined as a function of the duration of the person's normal respiration rate. Thus, in the case of an adult human, where the duration of a normal respiratory cycle is 5 seconds, the number of discrete measurement signals to be considered for the calculation of a continuous component of a set of discrete measurement signals may be equal to the number of discrete measurement signals required to cover a duration of approximately 5 seconds. At the ends of the sliding time windows, the moving mean is calculated over a smaller number of signals as the boundaries of the sliding windows are approached. A moving mean can also be calculated over a number of discrete measurement signals (300) in the range from 15 to 45. For example, if the frequency fE is equal to 10 Hz, a moving mean can be calculated with 45 discrete measurement signals (300). The moving mean calculated in this way for each discrete signal is subtracted from each discrete signal of a set of discrete measurement signals of the sliding time window in question (300) in order to provide a temporal sequence of useful discrete signals (400).

The method also comprises a step of generating at each final time $T_{f,i}$ an indicator of respiratory movements (410) calculated on the basis of a mean amplitude calculated over a set of useful discrete signals (400) included in a sliding time window with a length of $\Delta T_i$ preceding said time $T_{f,i}$ of the sliding time window numbered i. The analysis is therefore an analysis of discrete signals, instead of continuous signals. The signal is therefore analyzed by the determination of its amplitude, that is to say the size of the variation of its frequency, representing the amplitude of the respiratory movement. It is the size of the respiratory movement, not its frequency, that is the determining factor for the detection or non-detection of a respiratory movement. The frequency of respiration is taken into account in the definition of the sliding time windows. The method comprises a step of analyzing the amplitude of the signal, and the frequency of this amplitude is indirectly taken into account by the definition of the sliding time windows with a specified duration which follow each other and/or overlap according to a specified time interval, resulting in a more precise and comprehensive method. Thus, by using the method of the invention, it is possible to detect a low-amplitude respiratory movement, and to classify it as an absence of respiratory movement if the amplitude of this movement is below a predetermined threshold. It is thus possible to classify some low-amplitude respiratory movements, often synonymous with the presence of a problem, as representing an absence of respiratory movement. Thus, if a patient or an animal exhibits a low-amplitude respiratory movement, a warning can be given.

Depending on the value of a mean amplitude of a set of useful discrete signals (400) in a sliding time window with a length of $\Delta T_i$, the method will classify said time window in question either in the category of detection of a respiratory movement (500) or in the category of the absence of detection of a respiratory movement (600). The threshold of detection of a respiratory movement by calculation of the mean amplitude of a set of useful discrete signals included in a sliding time window with a length of $\Delta T_i$ is dependent on the noise generated by the measurement circuit (passive infrared detector, amplifier), and can therefore be determined empirically. Depending on the nature of the passive infrared detector and the associated operational amplifier, the threshold of detection of the presence of a respiratory movement may be determined, for example, by the execution of the method in controlled conditions. For example, if a Murata IRA-E700 passive infrared detector and an OPA2340UA amplifier are used, this threshold is in the range from 150 to 160 mV. The threshold of determination of the detection of a respiratory movement by calculation of a mean amplitude may therefore be set at 150 mV, 151 mV, 152 mV, 153 mV, 154 mV, 155 mV, 156 mV, 157 mV, 158 mV, 159 mV, or 160 mV. If the value of the mean amplitude is greater than or equal to this threshold, then a respiratory movement has been detected (500).

Preferably, in the step of generating at each final time $T_{f,i}$ an indicator of respiratory movements (410), this indicator is calculated on the basis of a mean amplitude calculated over a set of useful discrete signals (400) included in a sliding time window with a length of $\Delta T_i$ directly preceding said time $T_{f,i}$ of the sliding time window numbered i.

According to a preferred embodiment of the invention, the calculation of the mean amplitude in step v) of the method comprises the steps of:
- calculating an RMS amplitude value of a set of useful discrete signals (400) included in a sliding time window with a length of $\Delta T_i$,
- comparing said RMS value with a predefined threshold of detection of a respiratory movement, by the calculation of an RMS value.

The expression "RMS amplitude value" is to be interpreted as meaning the root mean square value of the amplitude, that is to say the root of the sum of squares divided by the number of elements in the sum.

The step of calculating an RMS amplitude value makes it possible to measure the oscillating component of a set of useful discrete signals (400) included in a given sliding time window, and thus to obtain a mean amplitude of the signal composed of the set of useful discrete signals (400) included in the given sliding time window. The threshold of detection of a respiratory movement by calculation of an RMS value is dependent on the noise generated by the measurement circuit (passive infrared detector, amplifier), and can therefore be determined empirically. Depending on the nature of the passive infrared detector and the associated operational amplifier, the threshold of detection of the presence of a respiratory movement may be determined, for example, by the execution of the method in controlled conditions. For example, if a Murata IRA-E700 passive infrared detector and an OPA2340UA amplifier are used, this threshold is in the range from 150 to 160 mV. The threshold of determination of the detection of a respiratory movement by calculation of an RMS amplitude may therefore be set at 150 mV, 151 mV, 152 mV, 153 mV, 154 mV, 155 mV, 156 mV, 157 mV, 158 mV, 159 mV, or 160 mV. If the RMS amplitude value is greater than or equal to this threshold, then a respiratory movement has been detected (500).

Figure 4:
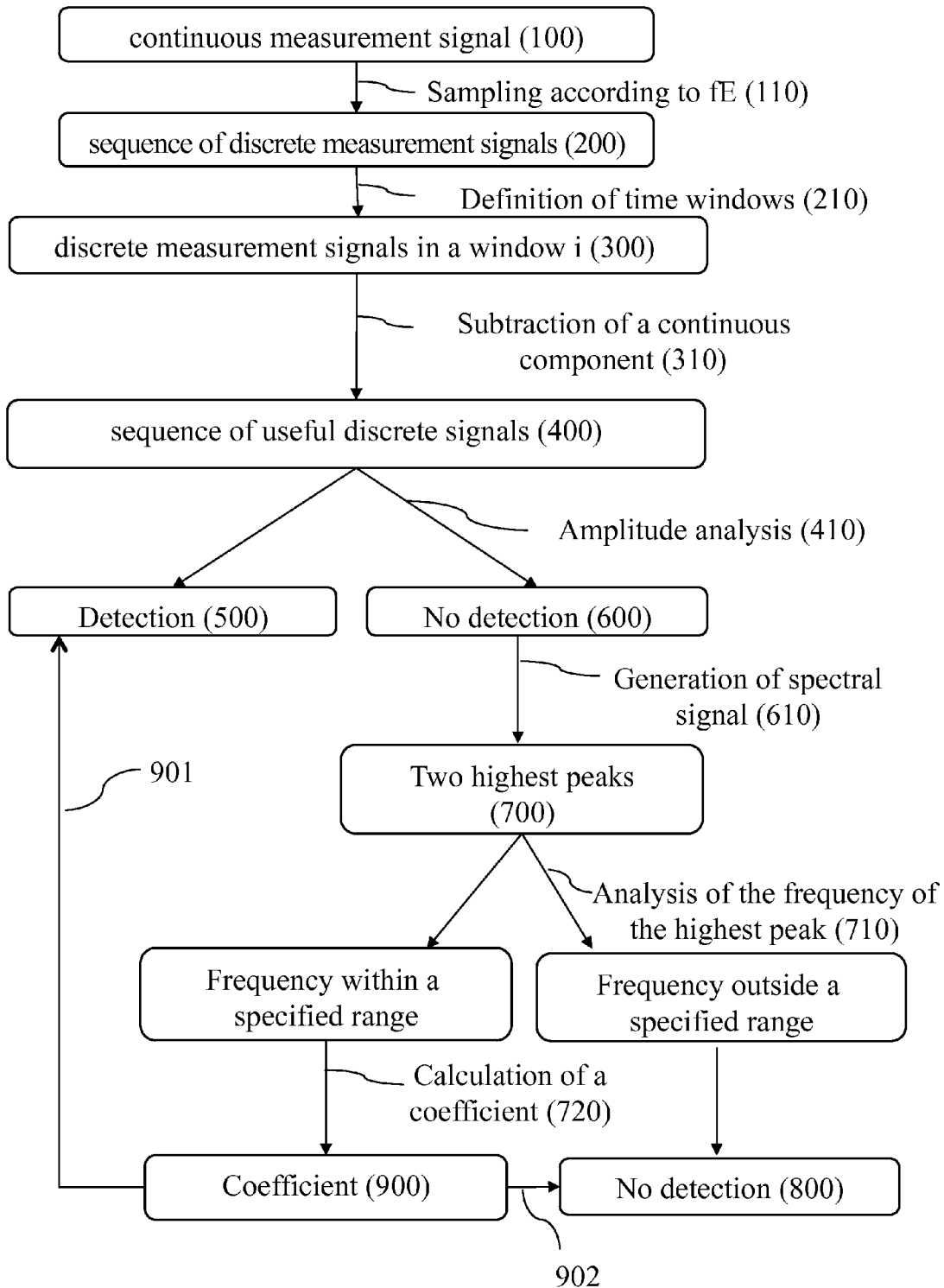
FIG. 4 shows, in a schematic manner, steps of a particular embodiment of the method according to the invention.

According to a preferred embodiment of the invention shown in FIG. 4, a supplementary step is provided. This step consists in:
- generating a spectral signal (610) of a set of useful discrete signals (400) included in a sliding time window with a length of $\Delta T_i$,
- determining the two highest peaks of said spectral signal (700),
- comparing (710) the frequency of the highest peak with a plausible frequency range of the respiratory movements,
- calculating (720) a coefficient (900) according to the formula:

$$\frac{(H1 - H2)^2}{Hx}$$

where
H1 is the amplitude of the highest peak,
H2 is the amplitude of the second highest peak,
Hx is the amplitude of the second highest peak if this amplitude is other than zero, or the amplitude of the highest peak if the amplitude of the second highest peak is zero,
- determining the presence of a respiratory movement by comparison between the coefficient (900) obtained in the preceding step and a predetermined threshold of detection of a respiratory movement by calculation of a coefficient. This supplementary step is provided for the purpose of analyzing a set of useful discrete signals (400) included in a sliding time window if the analysis of the mean amplitude does not enable the presence of a respiratory movement to be detected (600), and therefore if the mean amplitude is below the threshold of detection of a respiratory movement by calculation (410) of the mean amplitude of a set of useful discrete signals (400) included in a sliding time window. This is because the background noise may possibly be so great that the analysis of the mean amplitude cannot provide a usable result for certain sets of useful discrete signals included in a sliding time window. This step enables the presence of a respiratory movement to be distinguished even more clearly from the absence of a respiratory movement.

Thus, if a mean amplitude of a set of useful discrete signals included in a sliding time window is below the threshold of detection of a respiratory movement by calculation of the mean amplitude or by calculation of the RMS value (600), a spectral analysis (610) is performed on said set of useful discrete signals (400) included in a given sliding time window. This spectral analysis can be performed on the basis of any number of useful discrete signals (400). According to a preferred embodiment of the invention, a spectral analysis can be performed by means of a Fourier transform, in which case a number of signals equal to a power of two can be selected from among the set of useful discrete signals (400) included in a given sliding time window. This selection can be carried out in an arbitrary manner.

The frequency of the two highest peaks of said spectral signal is determined. If the frequency of the highest peak is outside a specified frequency range (710), the sliding time window in question is analyzed as an absence of detection of a respiratory movement (800). This specified frequency range (710) is a plausible frequency range for detecting respiration. For example, for an adult human the duration of a respiratory cycle, which may vary with the age and physiology of the person, is in the range from 1 to 5 seconds. In this case, the frequency range may be from about 0.20 Hz to about 1 Hz, or more preferably from 0.23 to 1.02 Hz. If the frequency of the highest peak is within said specified frequency range, a coefficient is calculated (720) according to the previous formula. If the result of the coefficient (900) is greater than or equal (901) to a specified value, the sliding time window in question is analyzed as the presence of a respiratory movement (500). If the result of the coefficient (900) is less (902) than a specified value, the sliding time window in question is analyzed as the absence of a respiratory movement (800). This coefficient (900) is determined empirically so as to eliminate erroneous detections without eliminating correct detections of a respiratory movement. This coefficient (900) may, for example, be equal to 10.

According to a preferred embodiment of the invention, a step consisting in:

determining, for each sliding time window i, whether a set of useful discrete signals (400) included in said sliding time window indicates the detection of a respiratory movement (500), if no sliding time window at a given time $T_{f,i}$ indicates the detection of respiratory movement (600 or 800), classifying said sliding time window i as containing no respiratory movement, if a specified number of successive sliding time windows are classified as containing no respiratory movement (600 or 800), triggering a visual and/or audible alarm, is provided.

For each of the one or more passive infrared detectors, each sliding time window is analyzed as detecting the presence of a respiratory movement (500), or the absence of a respiratory movement (600 or 800), at a given time $T_{f,i}$. If only one passive infrared detector is provided, the result of the analysis of a set of useful discrete signals (400) in a sliding time window corresponds to the detection or non-detection of a respiratory movement. If at least two passive infrared detectors are provided, each of the concomitant sliding time windows at a given time $T_{f,i}$ obtained from each of at least two passive infrared detectors is analyzed, and the most favorable result is retained for the set of the concomitant sliding time windows at the given time $T_{f,i}$. Thus, if only one sliding time window is classified as a detection of the presence of a respiratory movement (500), then the set of sliding time windows at the given time $T_{f,i}$ is classified as detecting the presence of a respiratory movement.

If all the concomitant sliding time windows at a given time $T_{f,i}$, or the only sliding time window at a given time $T_{f,i}$, are analyzed as signifying an absence of respiratory movement (600 or 800), then the whole set is classified as an absence of respiratory movement. After a specified number of successive sliding windows, if all the successive sets of concomitant sliding time windows at a given time $T_{f,i}$ and at each time interval are classified as an absence of respiratory movement (600 or 800), then a step of triggering a visual and/or audible alarm is provided. The number of successive sliding time windows required before said alarm is triggered is determined according to the duration of the time interval between each sliding analysis window, and according to the patient, so that an alarm is triggered when the duration of the absence of respiratory movement is considered abnormal. For example, in the case of an adult human, if the time interval between each sliding time window is 1 second, the number of successive sliding time windows may be in the range from 15 to 30, or preferably 20. A minimum period of time before the triggering of the alarm may be specified, depending on the species (human or animal). By way of example, if the respiratory movements of an adult human are monitored, this period of time may be in the range from 10 to 60 seconds, or from 10 to 45 seconds, or from 10 to 30 seconds, or from 20 to 30 seconds. Alternatively, this period of time may be 10, 15, 20, 25, 30, 35, 40, 45, 50, 55 or 60 seconds. Thus, if a period during which no sliding time window detects a movement is in the range from 10 to 60 seconds, or from 10 to 45 seconds, or from 10 to 30 seconds, or from 20 to 30 seconds, an alarm is triggered. This period of time may be predetermined according to a normal respiration rate of a person or an animal. In this case, the period of time may be equal to or greater than two normal respiration cycles of a person or an animal.

In a preferred embodiment of the invention, a step of processing a discrete measurement signal (200) is provided. This step consists in applying a median filter and an averaging (or low-pass) filter to said discrete measurement signals (200). This step makes it possible to eliminate excessive oscillations of the signal and excessively high frequencies, thus further improving the subsequent analysis of the useful discrete signal (400). For example, the median filter may consist in replacing each discrete measurement signal (200) with the median value of this discrete measurement signal, of the discrete measurement signal preceding it, and of the discrete measurement signal following it. Each discrete measurement signal is therefore converted to a median discrete measurement signal resulting from the application of a median filter to a plurality of successive signals. Preferably, the number of successive signals used to calculate the median value is 3, 5, 7, 9, 11, 13, 15, 17, 19 or 21. Even more preferably, the median value is calculated on the basis of three successive signals. A low-pass filter may, for example, consist in replacing each discrete measurement signal (200) with a mean calculated on the value of this discrete measurement signal, on that of the discrete measurement signal preceding it, and on that of the discrete measurement signal following it.

According to an even more preferable embodiment of the invention, shown in FIG. 2, at least one additional passive infrared detector (10), targeting a part of the body not capable of exhibiting respiratory movements or targeting the environment of a person, is provided. This at least one additional passive infrared detector (10) is used to supply, at a sampling frequency fE, a sequence of discrete background noise measurement signals, called the background signal, originating from said additional detector (10). This detector may be identical to the at least one passive infrared detector targeting a part of the body capable of exhibiting respiratory movements.

The at least one additional passive infrared detector (10) targeting a part of the body not capable of exhibiting respiratory movements or targeting the environment of a person may, for example, be aimed substantially perpendicularly to the at least one passive infrared detector (4) targeting a part of the body capable of exhibiting respiratory movements. The detection field of the additional passive infrared detector (10) targeting a part of the body not capable of exhibiting respiratory movements or targeting the environment of a person may have a detection field in the range from 30° to 45°. In other words, the detection field of the at least one additional passive infrared detector (10) targeting a part of the body not capable of exhibiting respiratory movements or targeting the environment of a person is not aimed toward a location on the patient capable of exhibiting respiratory movements. The sensitivity of the at least one passive infrared detector targeting a part of the body not capable of exhibiting respiratory movements or targeting the environment of a person may have a sensitivity equivalent to the at least one passive infrared detector (4) targeting a part of the body capable of exhibiting respiratory movements.

This preferred embodiment may include a step comprising the subtraction of a background signal, originating from the additional passive infrared detector (10) targeting a part of the body not capable of exhibiting respiratory movements or targeting the environment of a person, from a concomitant discrete measurement signal (200) originating from the passive infrared detector targeting a part of the body capable of exhibiting respiratory movements. The discrete measurement signal (200) generated in this way is then analyzed according to the various steps of the method described above.

The invention also relates to a device for monitoring the respiration of a person or an animal. This device, shown in FIG. 1, comprises:

at least one passive infrared detector (4) adapted to target at least one location on a patient (1) capable of exhibiting respiratory movements, at least one amplifier (6) for the at least one passive infrared detector (4), at least one signal processing means (7) programmed to execute a step of defining a series of N sliding time windows starting at different successive moments $T_{in,i}$ and having a length $\Delta_{Ti}$; a step of subtracting from each of said discrete measurement signals present in the same sliding time window a continuous component calculated over a plurality of these discrete measurement signals present in the same sliding time window, to obtain a temporal sequence of useful discrete signals; and a step of generating, at each final time $T_{f,i}$, an indicator of respiratory movements calculated on the basis of a mean amplitude of a set of useful discrete signals contained in a sliding window with a length of $\Delta T_i$, at least one visual and/or audible alarm (8).

These elements are interconnected by conventional connecting means (5) known to persons skilled in the art. The device may also comprise an analog/digital converter.

The discrete signal processing means (7) is connected to a luminous and/or audible alarm (8) which may be local or remote. This alarm device (8) is triggered by the signal processing means (7) if the latter detects no respiratory movements during a specified period of time according to the method.

According to a preferred embodiment of the invention, the device comprises a discrete signal processing means (7) programmed to execute the other steps of the method. Thus, the signal processing means (7) can be programmed to execute a step of subtracting a background signal from a discrete measurement signal. The signal processing means can be programmed to calculate an RMS value of amplitude of a set of useful discrete signals, and to compare said RMS value of amplitude with a threshold of detection by calculation of a mean amplitude. The signal processing means can also be programmed to generate a spectral signal from a set of useful discrete signals, to determine the frequency of the two highest peaks present in said spectral signal, to compare the frequency of the highest peak with a plausible predetermined frequency range of respiratory movements, to calculate a coefficient of amplitude comparison according to the formula:

$$\frac{(H1-H2)^2}{Hx}$$

where
H1 is the amplitude of the highest peak,
H2 is the amplitude of the second highest peak, and
Hx is the amplitude of the second highest peak if this amplitude is other than zero, or the amplitude of the highest peak if the amplitude of the second highest peak is zero, and to compare the coefficient of comparison of amplitude with a predetermined threshold of detection by calculation of a coefficient.

The device can also be programmed to classify a set of one or more sliding time windows as containing no respiratory movements and to trigger an alarm if a specified number of successive sliding time windows do not detect any respiratory movements.

According to an even more preferable embodiment of the invention, shown in FIG. 2, the device also comprises at least one additional passive infrared detector (10) targeting a part of the body not capable of exhibiting respiratory movements or targeting the environment of a patient.

An exemplary embodiment of some steps of the method is shown in FIGS. 5a and 5b. A plurality of time windows ($\Delta T_1$, $\Delta T_2$, $\Delta T_3$, $\Delta T_4$) follow each other according to a specified time interval (50). A sequence of discrete measurement signals (200) is generated by a passive infrared detector. For the window i in question, only the discrete measurement signals included in the time interval $\Delta T_i$ are analyzed. For each of these discrete measurement signals included in the window $\Delta T_i$, a continuous component (310) is calculated by calculating the mean of each discrete signal, of the discrete signal preceding it, and of the discrete signal following it. This continuous component (310) is subtracted from each discrete measurement signal (300), enabling a temporal sequence of useful discrete signals (400) to be obtained. For this sequence (400), the mean amplitude is calculated. The value of this mean amplitude is then compared with a detection threshold by calculating a predefined mean amplitude.

The invention can also be defined as relating to a method for determining the presence of a respiratory movement in a human or an animal. This method comprises the detection of movement by a passive infrared detector and the analysis of signals transmitted by this detector. The invention also relates to an apparatus for executing a method of detecting a respiratory movement.

The invention claimed is:

1. A method for monitoring the respiration of a patient, comprising the following steps:
   i) providing at least one passive infrared detector targeting at least one location on the patient capable of exhibiting respiratory movements,
   ii) providing, at a sampling frequency fE (110), at least one sequence of discrete measurement signals (200) originating from the at least one passive infrared detector,
   iii) defining a series of N sliding time windows (210), starting at different successive moments $T_{in,i}$, where i is an integer from 1 to N representing each sliding time window with a length of $\Delta T_i = T_{f,i} - T_{in,i}$, where $T_{f,i}$ denotes a final time of a sliding time window numbered i,
   iv) subtracting from each of said discrete measurement signals present in the same sliding time window (300) a continuous component calculated over a plurality of these discrete measurement signals (300) present in the same sliding time window, to obtain at least one temporal sequence of useful discrete signals (400),
   v) generating at each final time $T_{f,i}$ an indicator of respiratory movements (410), calculated on the basis of a mean amplitude calculated over a set of useful discrete signals included in a sliding time window with a length of $\Delta T_i$ preceding said time $T_{f,i}$ of the sliding time window numbered i.

2. The method as claimed in claim 1, further comprising a step consisting in:
   providing at least one additional passive infrared detector targeting at least one location on the patient not capable of exhibiting respiratory movements, or targeting the patient's environment,
   subtracting from the discrete measurement signals (200) of step ii) a background signal originating from the at least one passive infrared detector targeting at least one location on the patient not capable of exhibiting respiratory movements or targeting the patient's environment.

3. The method as claimed in claim 1 or 2, further comprising a step of calculating a mean amplitude comprising the steps consisting of:
  calculating an RMS amplitude value of a set of useful discrete signals (400) included in a sliding time window with a length of $\Delta T_i$,
  comparing said RMS amplitude value with a predefined threshold of detection of a respiratory movement by calculation of a mean amplitude.

4. The method as claimed in claim 3, further comprising a step consisting in:
  generating a spectral signal (610) of a set of useful discrete signals (400) included in a sliding time window with a length of $\Delta T_i$,
  determining the two highest peaks of said spectral signal (700),
  comparing (710) the frequency of the highest peak with a plausible frequency range of the respiratory movements,
  calculating (720) a coefficient (900) according to the formula:

$$\frac{(H1 - H2)^2}{Hx}$$

where
  H1 is the amplitude of the highest peak,
  H2 is the amplitude of the second highest peak,
  Hx is the amplitude of the second highest peak if this amplitude is other than zero, or the amplitude of the highest peak if the amplitude of the second highest peak is zero,
  determining the presence of a respiratory movement by a comparison between the coefficient (900) obtained in the preceding step and a predetermined threshold of detection of a respiratory movement by calculation of a coefficient.

5. The method as claimed in any one of the preceding claims, further comprising a step consisting in:
  determining, for a sliding time window, whether said set of useful discrete signals (400) included in said sliding time window indicates the detection of a respiratory movement (500),
  if no sliding time window indicates an absence of detection of a respiratory movement (600 or 800), classifying said sliding time window as containing no respiratory movement,
  if a predetermined number of successive sliding time windows are classified as containing no respiratory movement (600 or 800), triggering a visual and/or audible alarm.

6. The method as claimed in any one of the preceding claims, characterized in that the sampling frequency fE is in the range from 0.1 Hz to 50 Hz.

7. The method as claimed in any one of the preceding claims, characterized in that a median filter and a low-pass filter are applied to said temporal sequence of discrete measurement signals (200) of step ii).

8. The method as claimed in any one of the preceding claims, characterized in that a sliding time window has a length $\Delta T_i$ in the range from 5 to 20 seconds.

9. The method as claimed in claims 3 to 7, characterized in that the threshold of detection of a respiratory movement by calculation of a mean amplitude of a set of useful discrete signals (400) included in a sliding time window with a length of $\Delta T_i$ is in the range from 150 mV to 160 mV.

10. The method as claimed in claims 4 to 9, characterized in that the threshold of detection of a respiratory movement by a coefficient is greater than or equal to 10.

11. A device for monitoring the respiration of a person or an animal, comprising:
  at least one passive infrared detector (4) adapted to target at least one location on a patient (1) capable of exhibiting respiratory movements,
  at least one amplifier (6) for the at least one passive infrared detector (4),
  at least one signal processing means (7) programmed to execute steps iii), iv) and v) of claim 1,
  at least one visual and/or audible alarm (8).

12. The device as claimed in the preceding claim, characterized in that the signal processing means (7) is also programmed to execute a step of any one of claims 2, 3, 4, 5, 7 or 8.

13. The device as claimed in claim 11 or 12, characterized in that it includes at least one additional passive infrared detector (10), adapted to target a part of the body not capable of exhibiting respiratory movements or adapted to target the environment of a person.

* * * * *